US00PP16906P3

(12) United States Plant Patent
Delbard

(10) Patent No.: US PP16,906 P3
(45) Date of Patent: Aug. 1, 2006

(54) HYBRID TEA ROSE PLANT NAMED 'DELSTRIFRAM'

(50) Latin Name: *Rosa hybrida*
Varietal Denomination: Delstrifram

(75) Inventor: Arnaud Delbard, Malicorne (FR)

(73) Assignee: Société Anonyme des Pépinières et Roseraies Georges Delbard, Commentry (FR)

( * ) Notice: Subject to any disclaimer, the term of this patent is extended or adjusted under 35 U.S.C. 154(b) by 48 days.

(21) Appl. No.: 11/022,762

(22) Filed: Dec. 28, 2004

(65) Prior Publication Data

US 2006/0010535 P1 Jan. 12, 2006

(30) Foreign Application Priority Data

Jul. 12, 2004 (FR) ..... 18858

(51) Int. Cl.
*A01H 5/00* (2006.01)

(52) U.S. Cl. ..... Plt./132

(58) Field of Classification Search ..... Plt./130, Plt./132, 141, 143, 102
See application file for complete search history.

*Primary Examiner*—Howard J. Locker
(74) *Attorney, Agent, or Firm*—Buchanan Ingersoll PC

(57) ABSTRACT

A new and distinct variety of Hybrid Tea rose plant is provided which abundantly forms attractive double long lasting clear pink flowers that are striped with dark pink. The new variety is a whole plant mutation of the 'Delstriro' variety (U.S. Plant Pat. No. 13,086) which unlike the present variety forms clear red striped with dark red flowers. The growth habit is bushy. The vegetation is semi-vigorous to vigorous and good disease resistance is displayed when grown in a greenhouse. The new plant is well suited for forcing during cut flower production under greenhouse growing conditions.

1 Drawing Sheet

Figures 1, 2, 3, 4, 5, 6, 7, 8, 9, 10, 11, 12, 13, 14, 15, 16:
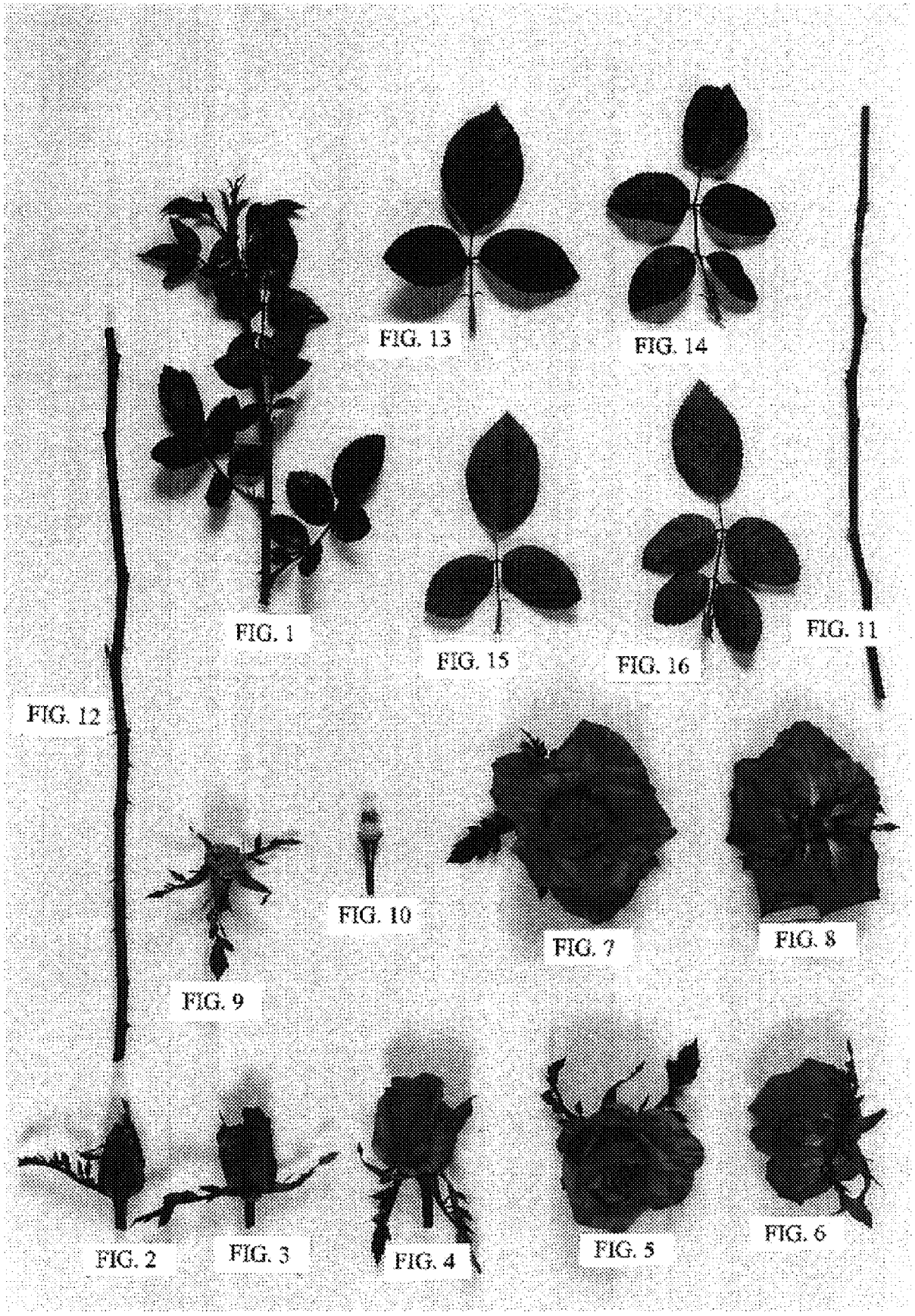

Botanical/commercial classification: *Rosa hybrida*/Hybrid Tea Rose Plant.
Varietal denomination: cv. 'Delstrifram'.

SUMMARY OF THE INVENTION

The new *Rosa hybrida* Hybrid Tea rose plant was discovered in a greenhouse at Malicorne, France, during 2003, and is a spontaneous mutation of unknown causation of the 'Delstriro' variety (U.S. Plant Pat. No. 13,086). Had the new variety of present invention not been discovered and preserved it would have been lost to mankind.

The parent 'Delstriro' variety was a spontaneous mutation of unknown causation of the 'Delego' variety (U.S. Plant Pat. No. 9,915) that was discovered during 1999 at Hyères, France.

It was found through careful study that the new variety of Hybrid Tea rose plant of the present invention exhibits the following combination of characteristics:

(a) from a physical point of view forms green mature wood, displays a bushy growth habit, and forms attractive double long lasting clear pink flowers that are striped with dark pink, and (b) from the biological point of view forms semi-vigorous to vigorous vegetation, produces flowers in abundance, exhibits the ability readily to be forced, and is resistant to diseases when grown under greenhouse conditions.

The new variety of the present invention forms medium length relatively straight stems, and rigid and substantially straight peduncles. An excellent ability to be forced under greenhouse conditions has been observed, as has a good vase life for its distinctive striped pink blossoms.

The new variety well meets the needs of the horticultural industry and is particularly well suited for growing in the greenhouse for the production of attractive long-lasting cut flowers which are clear pink striped with dark pink.

The new variety can be readily distinguished from other varieties in view of the combination of characteristics described herein. For instance, the new variety can be readily distinguished from its 'Delstriro' variety parent through an examination of the flower coloration. The 'Delstriro' variety forms red flowers that the striped with darker red. Also, the 'Delego' ancestor forms unstriped red flowers.

The new variety has been found to undergo asexual propagation and can be readily reproduced by conventional routes, such as budding (i.e., eye grafting), the rooting of cuttings, and tissue culture. This asexual reproduction as preformed at Malicorne, France, has demonstrated that the characteristics of the new variety are stable and are strictly transmissible from one generation to another.

The new variety has been named 'Delstrifram'.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown under glass in central France, at Malicorne, France.

FIG. 1—illustrates a specimen of a young shoot;

FIG. 2—illustrates a specimen of a floral bud at the opening of the sepals;

FIG. 3—illustrates a specimen of a floral bud at the opening of the petals;

FIG. 4—illustrates specimens of a flower in the course of opening;

FIG. 5—illustrates a specimen of an open flower—plan view—obverse;

FIG. 6—illustrates a specimen of an open flower plan view—reverse;

FIG. 7—illustrates a specimen of a fully open flower—plan view—obverse;

FIG. 8—illustrates a specimen of a fully open flower—plan view—reverse;

FIG. 9—illustrates a specimen of a floral receptacle showing the arrangement of the stamens and pistils;

FIG. 10—illustrates a specimen of a floral receptacle showing the arrangement of the pistils (stamens and sepals removed);

FIG. 11—illustrates a specimen of a flowering stem;

FIG. 12—illustrates a specimen of a main branch;

FIG. 13—illustrates a specimen of a leaf with three leaflets—plan view—upper surface;

FIG. 14—illustrates a specimen of a leaf with five leaflets—plan view—upper surface;

FIG. 15—illustrates a specimen of a leaf with three leaflets—plan view—under surface; and FIG. 16—illustrates a specimen of a leaf with five leaflets—plan view—under surface.

DETAILED DESCRIPTION

The chart used in the identification of the colors is that of The Royal Horticultural Society (R.H.S. Colour Chart—2001). The description is based on the observation of plants grown under glass in central France, at Malicorne, France.

Class: Hybrid Tea.

Plant:

*Height.*—Plants which were pruned to a height of 20 to 30 cm produce floral stems having a length of approximately 40 to 100 cm, and an average length of approximately 70 cm.

*Width.*—Approximately 50 to 60 cm.

*Habit.*—Bushy.

Branches:

*Color.*—Young shoots: when approximately 20 cm long, exhibit green coloration, Yellow-Green Group 146D. Floral stems: Yellow-Green Group 144A to 146B. Mature wood: Yellow-Green Group 146A.

*Diameter.*—Commonly approximately 8 to 11 mm (average 9 mm).

*Thorns.*—Configuration: convex on the upper edge and concave on the under edge. Quantity, length and frequency: on a typical floral stem having a length of 70 cm, there commonly are no thorns on the 30 cm below the bud, for the next 20 cm no or very few thorns, and for the last 20 cm some thorns irregularly arranged having lengths of approximately 3 mm to 1 cm and an average length of approximately 56 mm. On a young shoot having a length of approximately 30 cm, there commonly are no thorns. Color: on floral stems the coloration of the thorns is Greyed-Red Group 181A, and on mature wood the thorns are Greyed-Orange Group 165A and 165B.

*Leaves.*—Number: typical for the class and commonly number approximately 90 to 100. Size: Terminal leaflets commonly are approximately 60 to 90 mm (average 70 mm) in length and approximately 40 to 63 mm (average 46 mm) in width. Stipules: adnate, medium in size, and commonly 30 to 40 mm (average 35 mm) in length, approximately 7 to 9 mm (average 8 mm) in width at the mid-point, and approximately 18 to 22 mm (average 20 mm) at the distal end.

*Leaflets.*—Number: 3, 5, and 7. Shape: rounded to cordate at the base of the terminal leaflet and convex in cross section. Serration: present, single, and irregular. General appearance: consistent with medium glossiness. Petiole: commonly bears some prickles (often 1 to 3 per petiole), and the inner surface is grooved with non-glandular edges. Petiole color on young shoot: Greyed-Orange Group 173A with green and bronze coloration. Petiole color on floral stem: Yellow-Green Group 146A on the upper surface and Yellow-Green Group 146C on the under surface. Petiole color on mature wood: Yellow-Green Group 146A on the upper surface and Yellow-Green Group 146C on the under surface. Petiole length of terminal leaflet: approximately 16 to 22 mm, approximately 19 mm on average, with a standard deviation of 0.22 mm. Terminal leaflet length: approximately 60 to 90 mm, approximately 70 mm on average, with a standard deviation of 0.67 mm. Terminal leaflet width: approximately 40 to 63 mm, approximately 46 mm on average, with a standard deviation of 0.41 mm. Terminal leaflet shape at base: rounded. Leaflet color of young shoot: Yellow-Green Group 147A with some bronze coloration on the upper surface and Greyed-Purple Group 183C with some green coloration on the middle of the under surface. Leaflet color on floral stem: Green Group 139A on the upper surface and Yellow-Green Group 147B on the under surface. Leaflet color of mature wood: Yellow-Green Group 147A on the upper surface, and Yellow-Green Group 147B on the under surface. Venation: in a typical alternately arranged pattern, and the coloration commonly is Yellow-Green Group 151A at the distal end and Greyed-Yellow Group 160A at the proximal end.

Inflorescence:

*Number of flowers.*—Generally one per stem when grown under forced greenhouse conditions; however, sometimes during forced culture an axillary eye or eyes below the flower develop to form 1 or 2 flowers.

*Peduncle.*—Erect, stiff, Yellow-Green Group 144A in coloration with some small hairs, and approximately 85 to 115 mm in length (average approximately 100 mm).

*Sepals.*—Configuration: Two sepals commonly possess no extensions, and three sepals commonly possess medium to strong extensions. The extensions are denticulate and commonly are long to very long. The sepal length commonly is 50 to 70 mm (average 60 mm). Color: Yellow-Green Group 147B on the upper surface and Yellow-Green Group 146B on the under surface.

*Buds.*—Shape: ovate in longitudinal section just before the opening of the sepals. Size before calyx breaks: the bud lengths are approximately 28 to 31 mm, with an average length of approximately 30 mm. Color as calyx breaks: Yellow Group 2B striped with Red Group 38C. Size after calyx breaks: the bud lengths are approximately 38 to 45 mm, with an average length of approximately 40 mm. Color after calyx breaks: inside: Orange-Red Group 31A striped with Red Group 53A.

*Flower.*—Time: when growing in the greenhouse in the winter at a temperature of approximately 16 to 25° C.

flowering occurs in approximately 50 days. Shape: irregularly rounded when viewed from above. Form: double, flattened convex at the upper part when viewed from the side, and flattened convex to convex at the lower part when viewed from the side. Diameter: medium to large, approximately 10 to 12 cm, and approximately 11 cm on average, with a standard deviation of 0.5 cm. Petal number: commonly approximately 31 to 39, and an average of approximately 36. Petal size (second row from outside): the length is approximately 55 to 65 mm with a mean of approximately 59 mm, and a standard deviation of 0.4 mm; and the width is approximately 55 to 69 mm with a mean of approximately 53 mm, and a standard deviation of 6 mm. Petal shape: the first row of petals commonly exhibits a broad ovate configuration, the undulation of the petal margins is average, and the reflexing of the margins is average. Petal color: the following description of a nearly fully open flower was made while observing a rose grown in the greenhouse during October which had been undergoing opening for three days. Petal color (middle zone): on the inner surface Red Group 50C striped with Red Group 53C, and on the outer surface Red Group 50C striped with darker striping of Red Group 53C. Petal color (marginal zone): on the inner surface Red Group 50C striped with Red Group 53C, and on the outer surface Red Group 50C with darker striping of Red Group 53C. Petal spot at base: small in size, and can be absent when the plant is grown outdoors. Color of spot inner side: Yellow Group 9B. Color of spot outer side: Green-Yellow Group 1D. Stamens: approximately 136 in number and are somewhat regularly arranged. Filaments: medium in length, not all possess an anther, when the flower is partially open Yellow-Orange Group 14A in coloration, and when the flower is fully open Red Group 37C and Yellow Group 8B in coloration. Anthers: medium in size, all open at approximately the same time, and the immature coloration is Yellow-Orange Group 14C. Pollen: sparse in quantity and Yellow-Orange Group 21A in coloration. Pistils: approximately 147 in number. Styles: medium in length and Red Group 52A in coloration. Stigmas: Yellow-Orange Group 18B, and generally are present at the same level as the anthers, but a few anthers may be higher. Hips: rarely formed, in longitudinal section they are in the shape of a funnel and are approximately 23 mm in diameter. Seeds: none to date. Petal drop: the petals detach cleanly. Fragrance: slight. Lasting quality: long. When cut and placed in a vase, the flowers commonly last approximately 5 to 6 days.

Development:

*Vegetation.*—Semi-vigorous to vigorous.

*Blooming.*—Very abundant and almost continuous.

*Aptitude to forcing.*—Excellent.

*Resistance to diseases.*—Good under greenhouse conditions, as well as when grown outdoors.

*Winter hardiness.*—Not determined since the variety is primarily intended for cut flower production under greenhouse growing conditions.

*Drought tolerance.*—Not determined since the variety has been tested under standard greenhouse growing conditions with adequate water to date.

I claim:

1. A new and distinct Hybrid Tea Rose plant that exhibits the following combination of characteristics:

(a) from a physical point of view forms green mature wood, displays a bushy growth habit, and forms attractive double long lasting clear pink flowers that are striped dark pink, and (b) from a biological point of view forms semi-vigorous to vigorous vegetation, produces flowers in abundance, exhibits the ability readily to be forced, and is resistant to diseases when grown under greenhouse conditions;

substantially as illustrated and described.

* * * * *